United States Patent [19]

Ogunro

[11] Patent Number: 4,819,623

[45] Date of Patent: Apr. 11, 1989

[54] DEVICE TO FOSTER COSMETICALLY PLEASING HEALING OF NAIL BED TISSUE

[76] Inventor: E. Olayinka Ogunro, 625 Ray Ave., DeSoto, Tex. 75115

[21] Appl. No.: 782,318

[22] Filed: Oct. 1, 1985

Related U.S. Application Data

[63] Continuation-in-part of Ser. No. 605,112, Apr. 30, 1984, abandoned.

[51] Int. Cl.$^4$ .............................................. A61F 5/04
[52] U.S. Cl. ..................................... 128/87 A; 623/11
[58] Field of Search .................. 128/155, 81 A, 87 A; D24/33; 132/73; 623/54, 11; 604/158

[56] References Cited

U.S. PATENT DOCUMENTS

| Re. 31,886 | 5/1985 | Hodgson | 128/132 D |
| D. 265,507 | 7/1982 | Ogunro | D24/33 |
| 2,922,420 | 1/1960 | Cheuy | 604/158 |
| 3,987,499 | 10/1976 | Scharbach et al. | 623/22 |
| 4,181,127 | 1/1980 | Liushy | 128/155 |
| 4,406,023 | 9/1983 | Harris | 623/22 |
| 4,445,234 | 5/1984 | Ogunro | 128/81 A |
| 4,559,055 | 12/1985 | Ogunro | 623/11 |

FOREIGN PATENT DOCUMENTS 661624 11/1951 United Kingdom .................. 132/73

OTHER PUBLICATIONS

"A Study of Nail Bed Injuries: Causes Treatment & Prognosis" by Zook et al., The Journal of Hand Surgery, 3/1984.

Primary Examiner—Richard J. Apley
Assistant Examiner—James Prizant
Attorney, Agent, or Firm—Charles W. McHugh

[57] ABSTRACT

An article having the nature of a splint and/or mold which is adapted for temporary use on the injured digit of a person's hand or foot in order to foster beneficial healing after a nail plate has been removed. The splint includes a generally elongated sheet of thin (i.e., 0.020 inch) polypropylene or the like, which is inert to body fluids. It has a generally compound curvature so that it approximates the natural shape of a human nail plate, and has on its lower surface a smooth, concave shape which is adapted for contacting the healing nail bed. The sheet has a proximal end that is approximately perpendicular to the sides of said sheet, and the sheet has "square" corners which fit within the eponychial fold of the person's digit—for the purpose of preserving the fold and maintaining its size. The splint also has a structure depending from the two sides of the sheet for engaging the tissue of the person's nail bed; this structure holds the tissue and inhibits it from contracting significantly during healing of the nail bed. The healing nail bed is restricted to taking on the smooth shape of the juxtaposed sheet as it heals, and a healed nail bed will have a size that tends to be almost as large as its pre-injured size.

9 Claims, 2 Drawing Sheets

DEVICE TO FOSTER COSMETICALLY PLEASING HEALING OF NAIL BED TISSUE

REFERENCE TO RELATED APPLICATION

This publication is a continuation in part of case Ser. No. 06/605,112 filed Apr. 30, 1984 which has now been abandoned.

BACKGROUND OF THE INVENTION

This invention relates generally to structures useful in dealing with the results of diseases and/or injuries to the tips of a person's digits—on either the hand or foot. More specifically, it relates to structures having utility to foster healing of the ends of a person's digits, in order that nail plates (i.e., fingernails and toenails) can be restored to a condition that more nearly approaches their original condition.

It is well known that injuries to the ends of a person's digits occur frequently, and those injuries are often more than simply painful. That is, when a week-end carpenter strikes at a steel nail and hits his thumb instead, he may experience a pain that lasts for several minutes. But if he mishandles an electric saw and cuts himself, the initial pain may be only a small part of his overall problem—because a rotating saw blade that cuts through the top of a fingernail can cause damage that is not easily taken care of by the body's natural healing processes. Typically, when a person's nail plate has been cut off or it is so badly damaged that it must be surgically removed, the nail bed has been permitted to heal without the presence of any restraint. The result is typically an uneven and shrunken region of "scarry" tissue where there had once been a soft, smooth cushion of healthy tissue. Furthermore, the soft gauze dressings that are typically applied to a healing nail bed often become stuck to the healing tissue when blood or other body liquids dry in contact with the dressing. When a doctor later removes those dressings, the pain is often extreme—because an unprotected nail bed is one of the most sensitive spots on a person's body.

After a nail bed has healed, the nail plate will often grow back over the nail bed, assuming that at least some of the nail's root survived the injury. If the healed bed is not smooth and "natural," the nail that grows over that bed will be similarly deformed, and an irregular or split—and usually unpleasing—nail is the result. Examples of such deformed nails are illustrated at page 250 of an article by Zook, Guy and Russell entitled "A Study of Nail Bed Injuries: Causes, Treatment and Prognosis" that appeared in the March, 1984 issue of *The Journal of Hand Surgery*.

Attention has been given in recent years to cosmetic or reconstructive surgery for the purpose of replacing a damaged or disfigured nail with a prosthetic nail. And, two such examples of prosthetic nails are revealed in U.S. patents issued to this inventor, namely, U.S. Pat. No. Des. 265,507 entitled "Prosthetic Nail" which issued July 20, 1982 and U.S. Pat. No. 4,445,234 entitled "Prosthetic Nail" which issued May 1, 1984. No matter how beneficial these prosthetic nails may be for solving the cosmetic and functional problems of a missing nail, it would be preferable to foster the rehabilitation of a person's fingertips or toes without being forced to use a nail prothesis. And, it has now been concluded that the healing of a nail bed can be fostered by temporarily placing a particular kind of cover or splint over a damaged nail bed during the critical time that it is initially recovering from an injury. Such a cover must be smooth and in intimate contact with the nail bed and provide a sufficient restraint as to force the healing tissue to remain in an essentially normal condition, i.e., without irregular collagen. When the cover/splint of this invention is subsequently removed after a few weeks, the resulting nail that eventually grows back over the healed bed will appear much more smooth and will be less distinguishable from the person's ther, non-injured nails. This disclosure, therefore, is intended to present the details of a particular structure and the method of utilizing that structure—so as to enable a person skilled in the art to practice the invention.

Besides the cosmetic benefit that will be realized from use of the disclosed splint, an additional benefit will be realized from the physical protection of a tender area, especially during the first few days after a finger or toe has been damaged. With a temporary splint covering a freshly exposed nail bed, the risk of unplanned contact with nail bed tissue can be eliminated; and, any "point" pressure from contact with a pencil or the like can be distributed by a relatively firm splint so as to produce broader "area" pressure. It is another object of this invention, therefore, to protect a patient against unnecessary pain during those first several days after the injury.

The goal of minimizing pain when a patient tries to resume normal activities may seem like an adequate goal in and of itself, but another benefit from the use of the splint disclosed herein is a reduction in the amount of pain-killing drugs that the patient might otherwise feel is either necessary or desirable. And, it is now being more widely appreciated that pain-killing drugs should be used with the recognition that chemical dependency is a major threat to the full recovery of a patient. It should be appreciated, therefore, that the reduction of pain associated with a healing digit has both simple and complicated facets; and any structure which contributes to pain reduction is therefore doubly useful.

BRIEF DESCRIPTION OF THE INVENTION

In brief, the splint of this invention may be described as an article which is adapted for temporary use on the digits of a person's hand or foot in order to foster beneficial healing after a nail plate has been removed. The splint includes a generally elongated sheet which is inert to body fluids. It has a generally compound curvature so that it approximates the natural shape of a human nail plate, and has on its lower surface a smooth, concave shape which is adapted for contacting the healing nail bed. The sheet has a proximal end that is approximately perpendicular to the sides of said sheet, and the sheet has generally "square" corners which fit within the eponychial fold of the person's digit—for the purpose of preserving the fold and maintaining its size. The splint also has a structure depending from each of the two sides of the sheet for engaging the tissue of the person's nail bed; the purpose of this structure is to hold said tissue and inhibit it from contracting significantly during healing of the nail bed. The healing nail bed is restricted to taking on the smooth shape of the juxtaposed sheet as it heals, and a healed nail bed will have a size that tends to be almost as large as its pre-injured size. When the nail plate grows back over the healed bed, it will also be smooth and will look normal.

DESCRIPTION OF THE PREFERRED EMBODIMENTS

Figure 1:
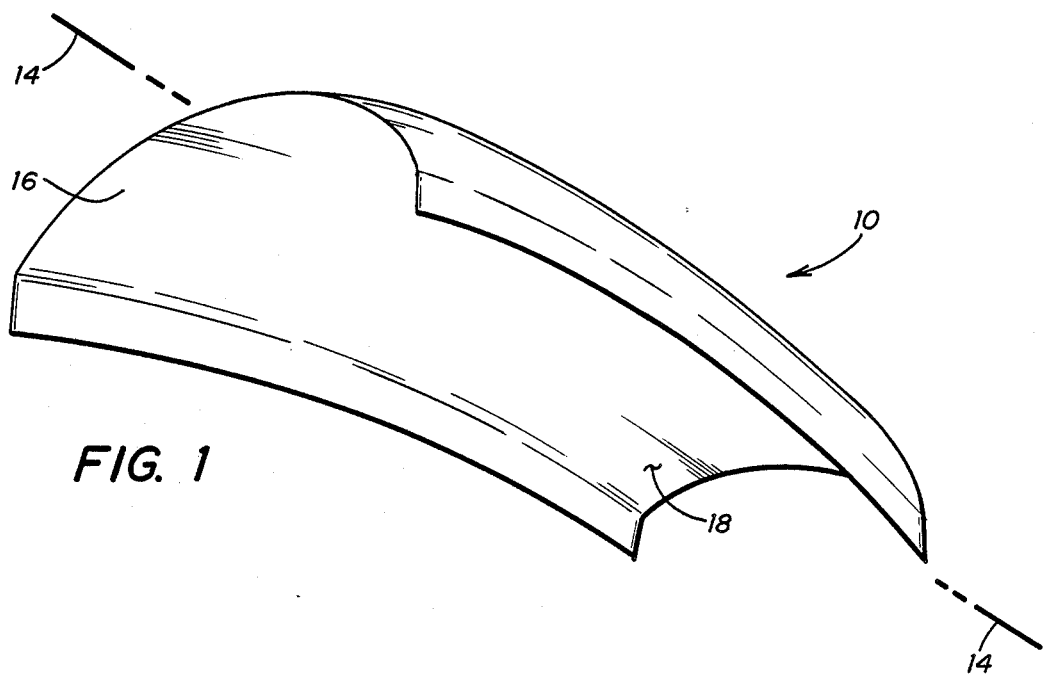
FIG. 1 is a perspective view of a splint in accordance with this invention, showing the generally concave underside of the splint.
Figure 2:
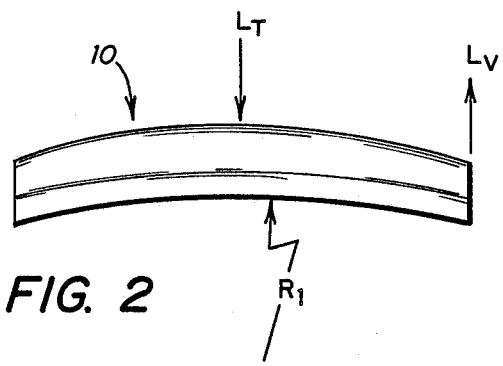
FIG. 2 is a side elevational view of the splint (drawn at a different scale), showing the curvature in a longitudinal plane.
Figure 3:
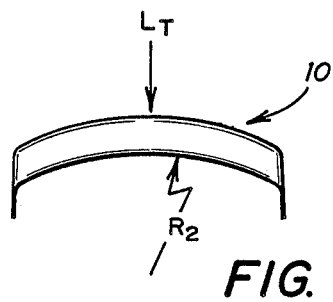
FIG. 3 is a front elevational view (which could also be called an end view) of the splint, on the same scale as FIG. 2.

Referring initially to FIGS. 1-3, the temporary splint for use on the digits of a person's hand or foot is shown in its simplest configuration. The splint 10 includes a generally elongated sheet 12 of firm but resilient material which is inert to body fluids and is water impervious. A preferred material for the sheet 12 is a polypropylene sold by Hercules Incorporated of Wilmington, Del. under the trademark "Profax 6253". The sheet 12 has a compound curvature so that it approximates the natural shape of a human nail plate. That is, the sheet has a first radius $R_1$ which defines a curve in a longitudinal plane; this first radius will usually be on the order of 1.5 inches. The sheet 12 also has a second radius $R_2$ which defines a curve in a transverse plane; this second radius is substantially smaller than $R_1$, usually about ⅓ thereof. The preferred transverse radius $R_2$ is about 0.4 inch, and the sheet 12 obviously appears somewhat like a segment of a cylinder when viewed along its longitudinal axis 14. The width of the sheet 12 as viewed along said longitudinal axis corresponds to a segment of a circle having an included angle of about 70 degrees.

The sheet's forward (distal) end 16 is preferably shaped the same as its proximal end. This offers an advantage to the surgeon in that there is no criticality as to which end is inserted into the eponychial fold. Besides having no "right" and "wrong" ends when the splint 10 is removed from a sterile package by the surgeon, it also will often be slightly long for most fingernails and toenails. A preferred length of about 1 inch permits some tolerance for error as the surgeon tries to match the shape of the injured digit—by trimming off small segments of the sheet. As long as the surgeon works by cutting away only small bits at a time, he might even be able to cut off and discard his first effort at shaping the distal end, while still leaving enough material in the sheet to start again with his shaping work—at either end of the symmetrical sheet.

The sheet's proximal end 18, both as manufactured and as installed, will preferably be relatively "square", in the sense that it will have two corners of approximately 90 degrees each. In this respect the splint 10 differs significantly from previously known appendages for nails—which are typically oval or elliptical in shape. Also, the thickness of the proximal end 16 is ideally the same thickness as the rest of the sheet 12, and should be at least thick enough to provide enough "body" to restrain or support the eponychial fold. This is important because a characteristic of the body's natural healing process is to eliminate the space between the eponychial fold and the nail bed, if some substantive material is not positioned within that space so as to keep it from closing. The "square" corners of the sheet 12 also inhibit the fold from contracting (in a transverse direction), which would cause the size of a healed nail bed to be unnecessarily reduced.

A preferred thickness for a sheet 12 is within the range of about 0.015-0.020 inch. A splint 10 having the shape illustrated in FIG. 1 and having the preferred dimensions (e.g., thickness of 0.020 inch, $R_1$ of 1.5 inches, $R_2$ of 0.4 inch) will have a surprisingly strong resistance to vertical loading in the direction indicated by the arrow $L_v$ in FIG. 2. In fact, it has been determined that a vertical lifting load $L_v$ of over five pounds can be imposed on the distal end of the splint 10 (when it is anchored at its proximal end) without causing the splint to bend. This is particularly advantageous because accidental loading of the splint 10 in the direction indicated by force $L_v$ can be imposed on a splint when the patient reaches for a cup, drawer, door latch, etc., and inadvertently strikes an immovable object. It is important, therefore, that the splint 10 have sufficient rigidity—based upon its geometry—to provide true protection during the critical healing period.

It may be instructive at this time to compared the splint 10 as described herein with previously disclosed attempts to providing temporary cover for healing tissue. The aforementioned article by Zook, et al entitled "A Study of Nail Bed Injuries: Causes, Treatments and Prognosis" describes techniques using either non-adherent gauze or 0.020 inch silicone sheet. It might be assumed that the silicone sheet will have more firmness than the gauze; but even silicone sheet is so soft, supple and flexible as to provide essentially none of the advantages that have been described herein. (Silicone sheet having a thickness of 0.020 inch may be thought of as having the firmness or "body" of the leather in a woman's kid glove; that is, such silicone sheet is very flexible.) An appropriate analogy might be to categorize Applicant's splint 10 as equivalent to a lobster's shell, while bandages and coverings of the prior art have had the flexibility of a cotton T-shirt. In fact, the splint 10 disclosed herein could even be utilized by the patient in scratching some skin that itches, if the patient should momentarily forget his injury and reach out to touch some spot—without remembering that he has been cautioned by his doctor against putting too much strain on the temporarily installed splint. The classical scratching process can also occur in what amounts to an inadvertent manner, if the patient is almost asleep and reaches out to touch some skin that is being irritated by a housefly or other insect. But as long as the sutures (which will usually be employed to anchor the distal end of the splint) can survive a scratching action, then the entire device will surely survive, because the curved sheet 12 has surprisingly strong properties.

In addition to its inherent strength, the splint's material and shape provide an advantageous spring constant. Three separate tests on a prototype of the splint have revealed that it has a spring rate of about 21 pounds per inch when loaded vertically, as indicated by the symbol $L_T$ in FIGS. 2 and 3, with the ends 16, 18 being unconstrained—as they would be when the splint is being worn by a patient. That is, the soft tissue of the eponychial fold will "anchor" the proximal end 18 of the splint 10 to the extent that it prevents the splint from moving vertically away from a digit; but the fold is too soft to prevent some longitudinal movement of the splint if the splint is subjected to loading in the direction indicated by $L_T$.

A distinguishing feature of the sheet 12 in this device is the gently concave and centrally unobstructed surface on the bottom of the splint 10, i.e., in the region under the splint that is adapted to contact the exposed tissue of the nail bed. This smooth, unobstructed surface contributes to an appearance that is markedly different from some earlier devices that have been disclosed by this inventor—in that there is no depending protuberance in the center of the sheet which could inhibit the smooth rehabilitation of the nail bed. In one sense, the splint 10 may accurately be considered to be like a template or mold, for the reason that the splint causes the healing tissue to take on the shape of the lower surface of the splint. But this characteristic is true only if the splint 10 is held securely against the top of the healing tissue. This is more nearly assured with the preferred material described elsewhere herein, because a few common sutures can be utilized to tie the distal end of the splint to the end of the digit. That is, a surgical needle will readily penetrate a sheet of 0.020 inch polypropylene, and the small hole created by the needle will not usually tear as a result of routine physical activity by the patient. So, with the distal end 16 secured by sutures and the proximal end 18 embedded within the eponychial fold, the splint 10 will usually remain on the digit for as long as the surgeon desires.

Figure 4:
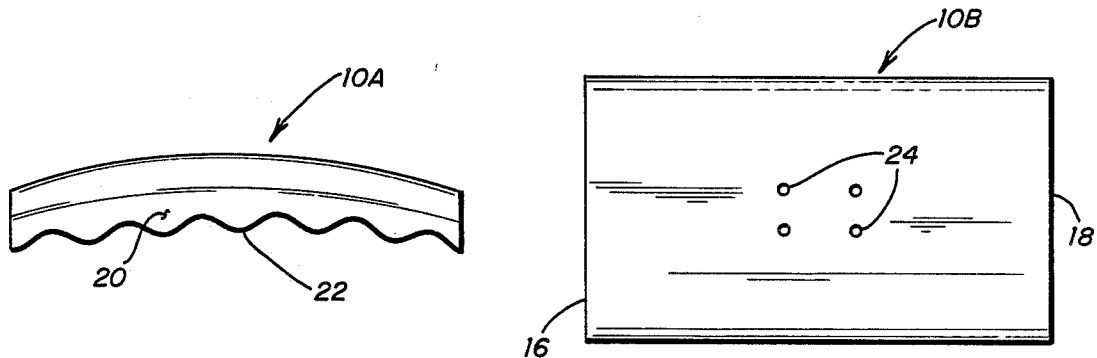
FIG. 4 is a side elevational view of another embodiment of the invention, clearly showing a non-linear edge along the visible side.

Somewhat greater assurance against unwanted longitudinal movement of an installed splint can be obtained by use of a configuration like that shown in Figure 4, wherein the edge 22 of the depending skirt or side 20 is non-linear, e.g., shaped like a sine wave. A saw-tooth configuration for the side edge would also be feasible, as would a square wave configuration; but it is believed that the sine wave configuration is likely to be more comfortable for the patient.

Figure 5:
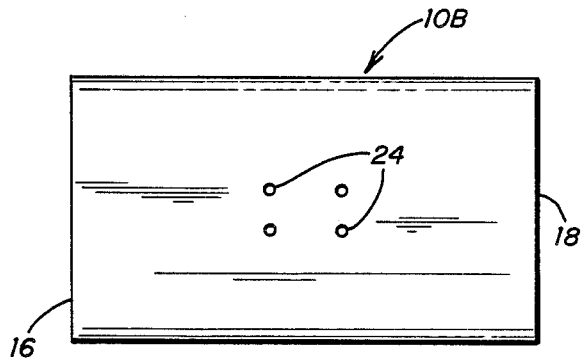
FIG. 5 is a top plan view of an embodiment of the invention having four "bleed" holes therein.

If the surgeon decides to leave the splint 10 on an injured digit for several days or even a few weeks, the splint—being impervious to liquids—conceivably could trap unwanted liquids under the splint. For this reason it is preferred to have one or more "bleed" holes in the central region of splint 10, so that liquids can drain spontaneously from under the splint. Four such holes 24 are shown in FIG. 5. In general, a large number of small holes (no larger than 1/16 inch diameter) are preferable to a small number of larger holes.

Figure 6:
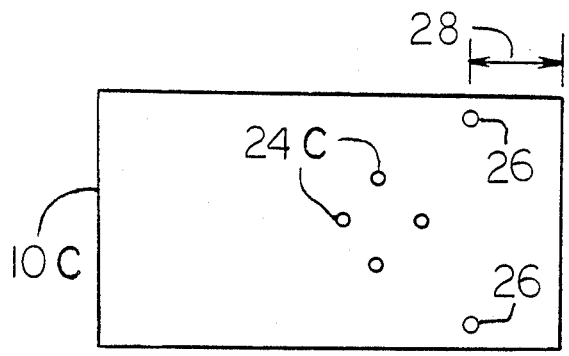
FIG. 6 is a top plan view of another embodiment of the invention, having both "bleed" holes and indicator holes—which aid a surgeon in correctly locating the splint on an injured finger.

Another embodiment of the invention is shown in FIG. 6, wherein the bleed holes 24C are arranged closer to one end of the splint 10C than to the other end, and wherein holes 26 are positioned near one end to unambiguously establish it as the proximal end of the splint. This embodiment offers an advantage over the earlier-described embodiment in that the two holes 26 can be utilized in two beneficial ways: (1) to receive sutures for anchoring the proximal end of the splint 10C to the digit; and (2) to provide visual confirmation that the splint 10C is adequately nested in the selcus. By placing the holes 26 at least 0.24 inch from the adjacent end of the splint (as indicated by the arrow 28), the holes will be just barely exposed when the proximal end is fully seated. (A typical eponychial fold will extend outwardly in a cantilevered fashion over a nail bed for about 0.2 inch.) If an inordinate gap should be visible between the distal edge of the eponychial fold and the holes 26, the surgeon will know that the splint 10C is not properly located; and if the surgeon does not act to retract the splint, it is likely that the sulcus will eventually collapse. Of course, a single centrally located aperture (instead of two apertures 26) would be as visible and would therefore serve the same "locating" function; but two spaced apertures are preferred, because they are capable of easily accepting two 5-0 nylon sutures for reliably anchoring the sheet to the digit. Another means for indicating when the proximal end of a sheet has been adequately inserted under an eponychial fold is a scribed or molded line on top of (or otherwise carried by) the sheet, at a distance equivalent to the location of the two apertures 26. But because bleed holes 24 are provided in the preferred embodiment, it will usually be easier to simply create additional holes in the plastic sheet at the same time that the holes 24 are created. Of course, it would be possible to establish the position of the indicator holes 26 so that they are expected to be just barely covered by the eponychial fold instead of just barely exposed; but this would be only an indirect way of confirming the absolute position of the splint—instead of the more direct way of placing the holes 26 where they can be seen (and measurements taken) at all times.

Figure 7:
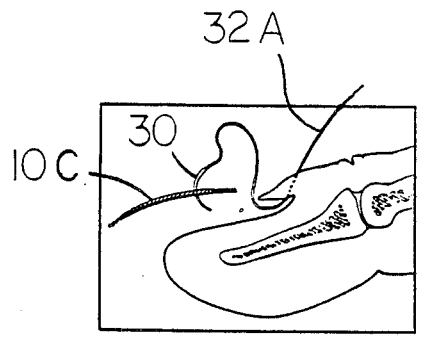
FIG. 7 is a side elevation view, partially cross-sectioned, showing the initial step of installing a splint on top of a nail bed that has been properly prepared (i.e., repaired to the extent possible and sterilized, etc.)
Figure 8:
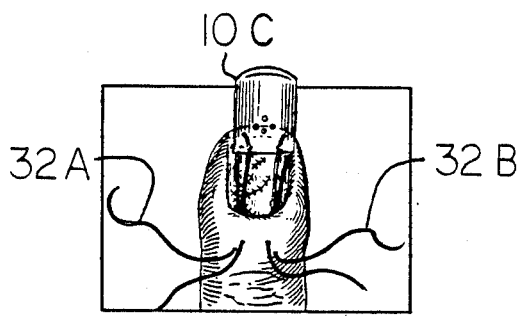
FIG. 8 is a top plan view of a splint in position above a patient's digit—just prior to tightening the sutures which will properly "seat" the splint against the sulcus.
Figure 9:
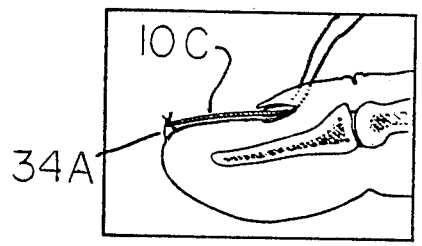
FIG. 9 is a side elevational view, partially cross-sectioned and similar to FIG. 7, showing the splint in its installed position.
Figure 10:
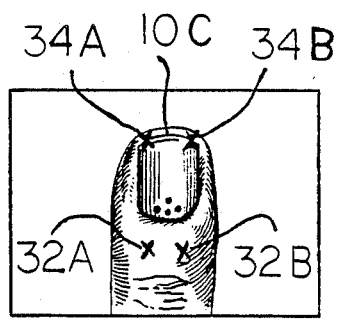
FIG. 10 is a top plan view of an installed splint with the sutures tied and trimmed.

To illustrate how one of the splints might be installed on an injured digit, FIG. 7 depicts the initial passage of a needle 30 through the eponychial fold and subsequently through the splint. Another suture 32B on the other side of the splint is then prepared, as shown in FIG. 8. When the sutures 32A, 32B are pulled tight, the proximal end of the splint will be securely nested into the sulcus (FIG. 9). Two forward sutures 34A, 34B, one at each distal corner (FIG. 10), help ensure that the sheet will not likely be pulled away (upwardly) from the healing nail bed, if the patient should drag his digit along some surface perpendicularly to the bed. After the nail plate has begun to grow outwardly from the sulcus for a sufficient distance, the surgeon will soon be able to observe this nail growth through the essentially transparent sheet; and when enough nail growth has been achieved under the splint, the surgeon will simply remove the sutures 32A, 32B, 34A, 34B and pull the splint forwardly and upwardly away from the nail bed.

Figure 11:
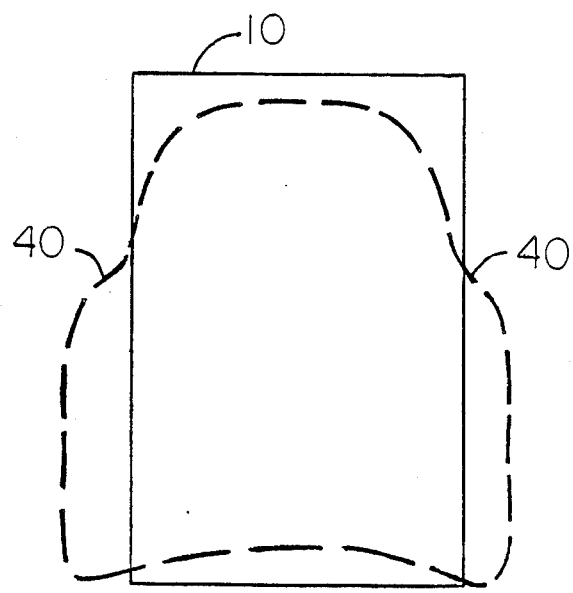
FIG. 11 is a top plan view of the splint of this invention superimposed on top of an exemplary prosthesis (e.g., the prosthesis shown in U.S. Pat. No. 4,445,234) so as to contrast the sizes of the two devices.

Perhaps at this point it might be advantageous to contrast the splints of this invention with the prosthesis shown in U.S. Pat. No. Des. 265,507 and U.S. Pats. Nos. 4,445,234 and 4,559,055. To this end, FIG. 11 shows the new splint 10 superimposed on top of an exemplary prosthesis. It will be seen that the prosthesis is markedly wider, and it has two sideward protrusions (shoulders) 40 that are intended to fit securely within two surgically prepared pockets at the sides of the digit. It is these shoulders 40 that inhibit the prosthesis from moving longitudinally—outwardly—with respect to a digit during normal activities. These shoulders are effective in a permanent prosthesis, but they would be of no benefit to a healing nail bed; and they would not likely prevent encroachment of tissue growth from the sides of the digit into the nail bed area. Furthermore, the depending elements that are shown in U.S. Pat. Nos. 4,445,234 or 4,559,055 would clearly interfere with the restitution of a smooth nail bed that is essential to the regeneration of a smooth nail plate. Hence, it should be apparent that the goals to be met with a temporary splint are significantly different than those that are to be satisfied with a permanent prosthesis; and the shapes/features of the two types of devices are consequently significantly different, too.

While only the preferred embodiments of the invention have been disclosed herein in substantial detail, it will be apparent to those skilled in the art that modifications thereof can be made without departing from the spirit of the invention. For example, it should be apparent that the splint disclosed herein is simultaneously accomplishing three separate functions: it is shaping the top of the nail bed as the bed heals; it is holding the sides of the nail bed apart, so that they do not unduly contract during healing; and it is keeping the eponychial fold intact, by preventing the fold from collapsing. However, it would be entirely feasible to accomplish one or more of these functions with elements that are not integrally formed—as is splint 10. Thus, the specific structures shown herein are intended to be exemplary and are not intended to be limiting, except as described in the claims appended hereto.

What is claimed is:

1. An article of manufacture adapted for temporary use in the manner of a splint on the digits of a person's hand or foot in order to foster beneficial healing promptly after a nail plate has been removed, comprising:
    (a) a generally elongated sheet of thin but substantially rigid plastic material which is generally rectangular when seen in a plan view, and said sheet being inert to body fluids and being essentially transparent, and having a curvature so that it approximates the natural shape of a human nail plate, and said sheet having a first radius which defines a curve in a longitudinal plane and a second radius which defines a curve in a transverse plane, and the transverse radius being appreciably less than the longitudinal radius, and the width of the sheet between its two sides corresponding to approximately a 70 degree segment of the circle defined by the transverse radius, and the sheet having a smooth, concave and substantially uninterrupted lower surface that is adapted for being installed so that it is in contact with and covers the nail bed, and the sheet having a proximal end that is approximately perpendicular to the sides of said sheet, whereby the proximal end of the sheet is adapted to fit under the eponychial fold of the person's digit for the purpose of preserving said fold during the healing of the nail bed; and
    (b) means depending from the two sides of said sheet for engaging the tissue of the person's nail bed so as to hold said tissue and inhibit it from contracting significantly during healing of said nail bed, whereby the healing nail bed is restricted to taking on the smooth shape of the juxtaposed sheet as it heals, and whereby a healed nail bed has a size that tends to be almost as large as its pre-injured size, and whereby a new nail plate will tend to be as smooth as the sheet when the nail plate progressively grows underneath the sheet and over the healing nail bed.

2. The article as claimed in claim 1 wherein said means for engaging the tissue of the nail bed constitutes a depending skirt which extends for essentially the full length of each of the two sides of the sheet, and each such skirt having a length of about 1 inch.

3. The article as claimed in claim 1 wherein the corners between the proximal end of the sheet and the sides of the sheet have an included angle of approximately 90 degrees.

4. The article as claimed in claim 1 wherein the sheet has a plurality of centrally located apertures that are sized and positioned to permit the drainage of body liquids from under the sheet during the body's healing process, and said apertures being no greater than about 1/16 inch in diameter, whereby the healing nail bed is restrained over nearly all of its upper surface.

5. The article as claimed in claim 1 and further including a locating means provided within the plane of said sheet for indicating when the proximal end of the sheet has been inserted under the eponychial fold for a sufficient distance, whereby the risk of collapse of the sulcus may be minimized by virtue of inserting the sheet a sufficient distance under the eponychial fold.

6. The article as claimed in claim 1 and further including a locating aperture in the sheet which is positioned about 0.24 inch from the proximal end of the sheet, whereby said aperture will be adjacent the eponychial fold but will still be visible when the proximal end of the sheet is fully seated below the eponychial fold of the person's digit.

7. The article as claimed in claim 6 and further including a second locating aperture in the sheet which is aligned with the first aperture, and one of said apertures being positioned near one side of the sheet and the other aperture being positioned near the other side of the sheet, and the apertures being sized to readily receive a 5-0 nylon suture, whereby the locating apertures may serve a dual purpose in locating the sheet and assisting in securing the sheet to the person's digit.

8. The method of fostering the smooth healing of an injured nail bed on a person's digit, comprising the steps of:
    (a) temporarily securing to the top surface of the injured nail bed a thin but substantially rigid structure made of artificial and sterilizable material, the structure lying in intimate contact with the tissue of the injured nail bed over nearly all of its upper surface, and the tissue-contacting surface of said structure being smooth and generally concave so that it will form an effective template to mold the healing nail bed;
    (b) restraining the sides of the healing nail bed in order that said nail bed does not contract as it heals; and
    (c) maintaining the eponychial fold of a person's digit by inserting the proximal end of said rigid structure under said fold so as to prevent it from collapsing until such time as the patient's nail plate can naturally reconstruct itself.

9. The method as claimed in claim 8 wherein all three of the recited steps are simultaneously accomplished by a single, integral structure.

* * * * *